US008584836B2

(12) United States Patent
De Waleffe

(10) Patent No.: US 8,584,836 B2
(45) Date of Patent: Nov. 19, 2013

(54) CONDOM WRAPPING

(76) Inventor: Xavier De Waleffe, Montigny-le-Tilleul (BE)

(*) Notice: Subject to any disclaimer, the term of this patent is extended or adjusted under 35 U.S.C. 154(b) by 0 days.

(21) Appl. No.: 13/509,575

(22) PCT Filed: Nov. 3, 2010

(86) PCT No.: PCT/EP2010/066755
§ 371 (c)(1),
(2), (4) Date: May 11, 2012

(87) PCT Pub. No.: WO2011/057931
PCT Pub. Date: May 19, 2011

(65) Prior Publication Data
US 2012/0222974 A1    Sep. 6, 2012

(30) Foreign Application Priority Data

Nov. 13, 2009  (LU) .......................................... 91622

(51) Int. Cl.
*B65D 85/08* (2006.01)
(52) U.S. Cl.
USPC ............................. 206/69; 383/200; 383/207
(58) Field of Classification Search
USPC ............ 206/69, 802, 484, 233; 383/210, 200, 383/207; 128/844
See application file for complete search history.

(56) References Cited

U.S. PATENT DOCUMENTS

| | | | | | |
|---|---|---|---|---|---|
| 1,543,865 | A | * | 6/1925 | Muchmore | 221/63 |
| 4,875,491 | A | * | 10/1989 | Parrone | 128/844 |
| 5,044,492 | A | * | 9/1991 | Auerbach | 206/69 |
| 5,316,019 | A | * | 5/1994 | Jones | 128/844 |
| 5,482,053 | A | * | 1/1996 | Kelly | 128/844 |
| 5,524,759 | A | * | 6/1996 | Herzberg et al. | 206/494 |
| 5,531,230 | A | * | 7/1996 | Bell | 128/842 |
| 5,666,972 | A | * | 9/1997 | Gifford | 128/842 |
| 6,257,410 | B1 | * | 7/2001 | Ulmann et al. | 206/389 |
| 6,616,334 | B2 | * | 9/2003 | Faaborg et al. | 383/211 |
| 2009/0241966 | A1 | * | 10/2009 | Gray et al. | 128/844 |

FOREIGN PATENT DOCUMENTS

| | | | |
|---|---|---|---|
| DE | 3939679 | A1 * | 5/1991 |
| DE | 20014263 | U1 | 12/2001 |
| DE | 20215481 | U1 | 2/2003 |
| EP | 0604675 | A1 | 6/1994 |
| JP | 51155277 | U | 12/1976 |
| JP | 62125521 | U | 10/1987 |
| JP | 63133210 | U | 8/1988 |
| JP | 63195822 | U | 12/1988 |

OTHER PUBLICATIONS

Preliminary Report on Patentability from PCT/EP2010/066755, issued by the European Patent Office on Feb. 13, 2012. Report is in French however the translation was sent directly to the United States Patent and Trademark Office by the European Patent Office.

* cited by examiner

*Primary Examiner* — David Fidei
(74) *Attorney, Agent, or Firm* — James E. Walton; Damon R. Hickman

(57) ABSTRACT

The invention allows unwrapping without stress, including in the dark, and the assured taking of the condom in the right orientation, without risk of inversion, without risk of contaminating contact with the exterior of the condom, with no risk of the condom falling from the wrapping during opening, without risk of tearing the condom with the teeth or a cutting object during unwrapping.

13 Claims, 2 Drawing Sheets

CONDOM WRAPPING

BACKGROUND OF THE INVENTION (1) Field of the Invention

The invention relates to a condom wrapping (2) Description of Related Art

For various reasons of hygiene and safety, condoms are wrapped individually. The wrappings typically consist of two superposed leaves of flexible film welded at the edges forming a hermetic seal. The rolled-up condom is contained therein with the vessel adjacent to the internal surface of one of the film leaves. This sort of wrapping normally includes a notch in the edge, permitting the user to commence the tear to open the wrapping and extract the condom. Most of these wrappings do not allow the identification of the orientation of the condom at the moment of its extraction from the wrapping. In fact, these wrappings are symmetrical, the outside surfaces of the film leaves are identical and so the orientation of the condom cannot be ascertained before opening.

In fact condoms do have an orientation as they are packed rolled up from the lower edge towards the vessel. Even though a condom is reversible and theoretically can be used either way around, it is imperative to place the condom on the tip of the penis in the right orientation to permit its unrolling to the base in the opposite direction to that in which it was rolled up. In its rolled-up form the condom is annular or in the shape of a ring corresponding to the rolled up cylindrical part, with the vessel in the centre of this ring shape. Owing to the extreme flexibility of the condom, the vessel can easily be inverted when the condom is handled, meaning that it can be oriented either way relative to the general lay of the annular part. It is therefore quite difficult to identify the correct orientation of the condom once it is held by the annular part, in particular in the dark. An attempt to place the condom the wrong way up will render it unusable or engender a risk of contamination owing to the fact that it must be reversed and repositioned after being in contact with the penis. Various solutions to this problem have been developed.

The document for patent WO 98/46495 allows for a central line of weakness on each of the two leaves of the wrapping and two small loops placed parallel with the lines of weakness on the exterior edges of one of the leaves. Therefore the user can, in theory with a single hand, open the wrapping by holding the pack in one hand at the level of the line of weakness and then by an extension of the thumb engaged with one of the loops create the force to separate the two parts divided by the central line of weakness. As the loops are on one surface only the opening can theoretically always be on the same side of the condom, which may guide the user. However this solution presents two major drawbacks, namely that the hand movement is quite complex, requiring a certain dexterity, and the fact that the condom is grasped by the annular part, allowing the loss of the orientation of the condom once it is extracted from the part of the wrapping which remains in the hand.

The document for patent DE 200 14 263 U1 addresses the problem identified above and proposes as a solution a wrapping fitted with a cartridge of compressed air directed towards the interior of the vessel in such a way that it presents itself clearly on opening the wrapping. Although it is interesting, this wrapping is complex and costly to make.

The document for patent EP 0 604 675 A1 also addresses the problem mentioned above and proposes as a solution a wrapping containing a series of small ribbons distributed on the exterior edge of the annular part of the condom in its rolled-up state, these ribbons having been rolled up with the condom and attached to the wrapping. The placing of the condom is achieved by approaching the tip of the penis with the wrapping and exerting a force on the lower face of the packaging by means of a movement of the wrapping. The lines of weakness on each face of the wrapping part, forming an aperture for the penis and the condom unrolls automatically by continued movement of the wrapping and the ribbons which assist the unrolling of the annular part. Although seeming efficient this solution is costly and complex and has a major drawback in terms of comfort and hygiene.

BRIEF SUMMARY OF INVENTION

The objective of the invention is to propose a condom wrapping resolving the problems mentioned above whilst mitigating at least one of the drawbacks mentioned above.

The invention consists of a condom wrapping comprising two superposed sections of flexible film joined at the edges forming a container for the rolled-up condom with the vessel of the condom in its normal position adjacent to the internal surface of one of the sections of film and the direction of unrolling of the condom oriented to the other section of film, the section of film adjacent to the vessel of the condom containing a first line of weakness in the general shape of the contour of the condom and describing an opening area; and a means of grasping the part of the film outlined by the line of weakness; in a way that such part of the film might be torn in order to open the wrapping on the side of the vessel of the condom. The invention allows unwrapping without stress, including in the dark, and the assured taking of the condom in the right orientation, without risk of inversion, without risk of contaminating contact with the exterior of the condom, with no risk of the condom falling from the wrapping during opening, without risk of tearing the condom with the teeth or a cutting object during unwrapping.

In one advantageous embodiment of the invention, the contour of the first line of weakness and the contour of the condom are generally circular and the diameter of the contour of the line of weakness is smaller than that of the condom, preferably 1-10% smaller, in such a way as to maintain the condom in its wrapping after opening, whilst permitting the easy extraction of the condom, without its unrolling, by traction on the vessel.

In a further advantageous form of the invention, the section of film adjacent to the vessel of the condom has at least one additional line of weakness extending from the first line of weakness away from the opening area, radiating generally from the circular contour of the first line of weakness. These optional additional lines of weakness serve to facilitate the extraction of the condom.

In yet another advantageous embodiment of the invention, the section of film adjacent to the vessel has several, preferably four, additional lines of weakness distributed uniformly radiating from the contour of the first line of weakness.

In yet another advantageous form of the invention the means of gripping are such that they allow the section of film adjacent to the vessel to be identified by touch. Unwrapping the condom can therefore be achieved in total darkness owing to dependable tactile recognition.

In a further advantageous embodiment of the invention, the means of gripping include markings visible in the dark, preferably phosphorescent markings. Unwrapping the condom can therefore be achieved in total darkness owing to visual recognition.

In yet another advantageous form of the invention the means of gripping comprise of a tab connected to the part of the film outlined by the first line of weakness, the tab preferably being connected to that part of the film at the level of the line of weakness, so as to optimise purchase during the pulling of the tab.

In another advantageous embodiment of the invention the tab is connected to the part of the film outlined by the line of weakness by gluing or soldering.

In another advantageous form of the invention the tab is a piece of film similar to the film from which the rest of the wrapping is made.

In another advantageous embodiment of the invention the first and/or additional lines of weakness are created by means of one of the following processes: milling, weakening by laser beam, perforation, cutting, chemical treatment.

In another advantageous form of the invention the contour of the first line of weakness is open so as to retain the part of the film outlined by the first line of weakness attached to the rest of the wrapping after opening. By this means the wrapping remains in one piece, i.e. forms a single item of scrap, which reduces the risk of dispersal of small scraps.

In another advantageous embodiment of the invention the contour of the first line of weakness is closed so as to assure the separation of the part of the film outlined by the first line of weakness after opening.

BRIEF DESCRIPTION OF THE SEVERAL VIEWS OF THE DRAWINGS

In another advantageous form of the invention the wrapping includes the condom.

Other characteristics and advantages of the present invention will be better understood with the aid of the description and drawings including.

DETAILED DESCRIPTION OF THE INVENTION

Figure 1:
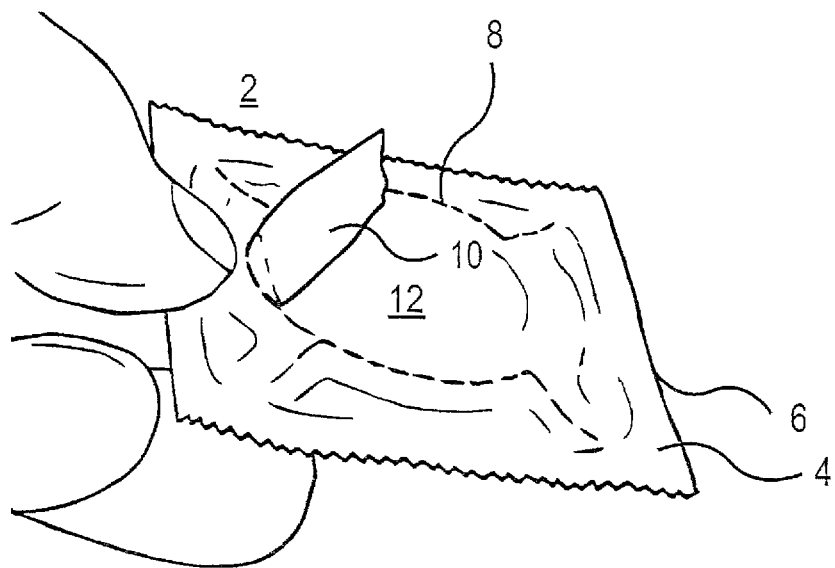
FIG. 1 is a perspective view of a condom wrapping according to the invention.

The envelope of the wrapping 2 is composed of two superposed composite leaves 4 and 6 welded, holding the rolled-up lubricated condom 12. Leaves 4 and 6 are in principal identical with respect to their shape and material. The top leaf 4 is however distinct in the following ways:
Pre perforation 8 of an opening for unwrapping
Tab 10, allowing
  The location of the wrapped condom in a dark environment by visual means;
  The easy detection of the orientation of the condom by tactile means
  The easy opening of the wrapping
Phosphorescent markings (optional)

Within the wrapping the exterior part of the vessel of the rolled condom is oriented towards leaf 4, equipped with the distinctive signs cited above.

The wrapping opens exclusively and easily by the 'uncapping' of part of the identifiable leaf.

This leaf surface has pre-cut line 8 allowing the tear to follow a set path.

The path of the tear is a near-complete circle of slightly smaller diameter than that of the rolled condom.

From the four corners pre-cut lines 14 start diagonally at the edge of the wrapping and pass to the boundary of the pre-cut circle.

Attached by adhesive or soldering to pre-cut circle 8 is a strong tab 10, of sufficient size to be easily gripped between the thumb and forefinger and the extremity of which may be textured and may be printed with phosphorescent markings.

Tab 10 is made of an untearable leaf of composite aluminium and plastic.

The solder or gluing of the tab has a break strength in excess of the resistance to tearing of the pre-cut multi-layer leaf of the envelope (see below).

The tab is positioned between the centre and the circumference of the pre-cut circle or exclusively on the border of the circumference, being the most appropriate place to assure the best tear along the pre-cut circle when the tab is pulled between the thumb and index finger.

At the opposite side of the circumference from the tab or at the side opposite the part of the circumference closest to the tab if the tab is nearer the centre, the circle is not pre-cut along approximately one quarter its circumference, between beginnings of the two diagonals.

Holding the wrapping between the thumb and index finger of one hand, whether left-handed or right-handed, one can easily discern the tab on one side, including in the dark and by means of touch only.

Figure 2:
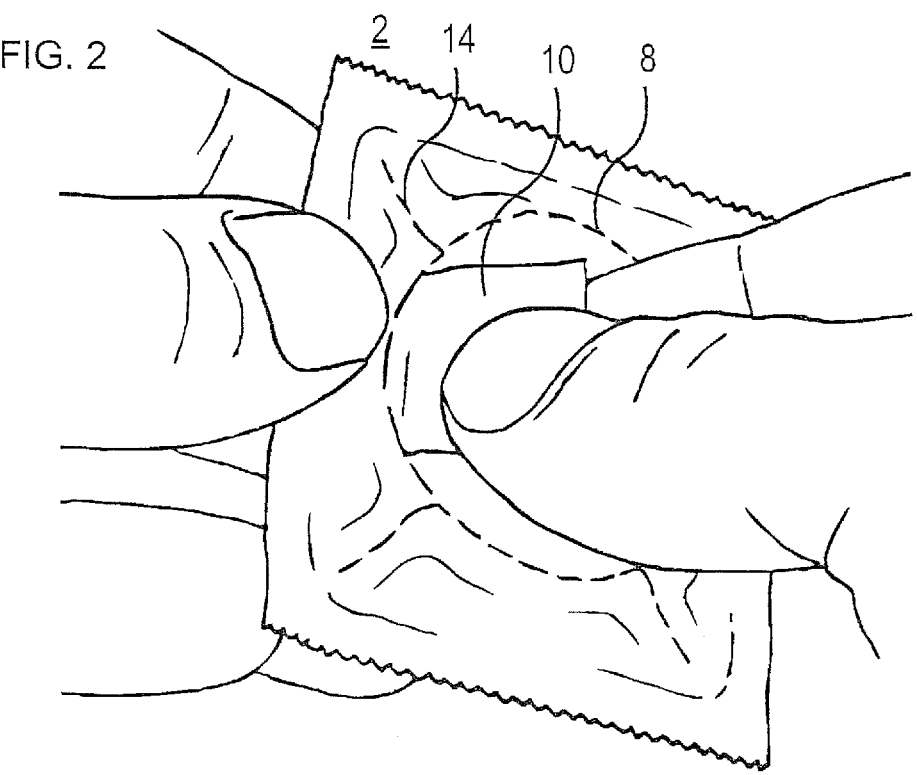
FIG. 2 illustrates the first step in the process of opening the wrapping as in FIG. 1.
Figure 3:
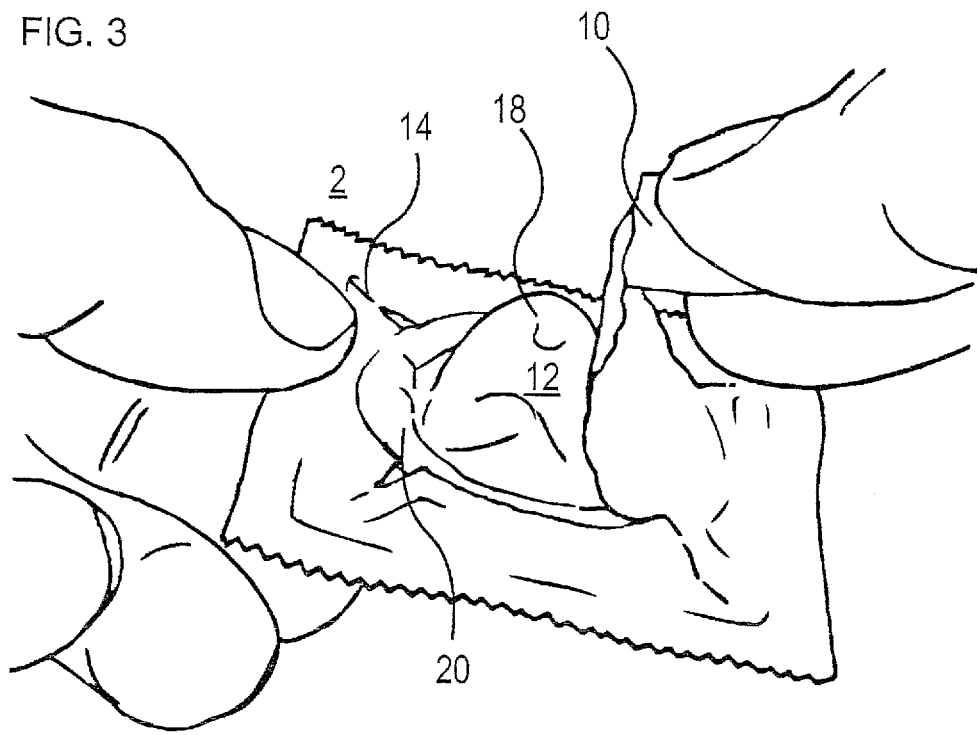
FIG. 3 illustrates the second step in the process of opening the wrapping as in FIG. 1.
Figure 4:
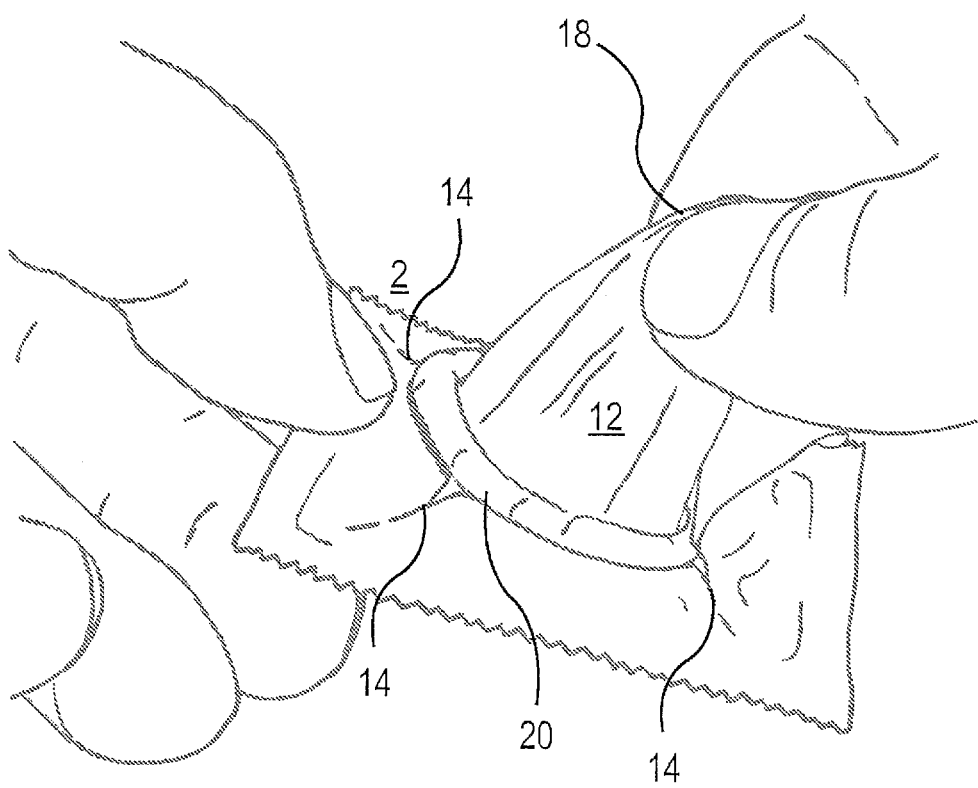
FIG. 4 illustrates the third step in the process of opening the wrapping as in FIG. 1.

Whilst the edge of the wrapping can be held between the thumb and index of one hand and the grip tab can be held between the thumb and index of the other, it is certain that the condom will be unwrapped in the correct orientation, i.e. that the vessel 18 will be facing upwards when the wrapping is opened. To open, all that is required is to pull the hands in opposite directions as shown in FIG. 2 and the top leaf will tear following the circle as illustrated in FIG. 3. The condom is uncovered, vessel 18 upwards. The condom does not fall from the wrapping because the diameter of the opening is very slightly smaller than the diameter 20 of the rolled condom. To remove the condom, still holding the wrapping in one hand release the tab from the other and grasp the condom by its vessel, as shown in FIG. 4. Up to this point the condom is held in the wrapping and cannot fall or slip out. Once the condom is grasped by the vessel 18 all that is required is to pull, the pre-cut diagonals can open and release the condom, only if it is held by the vessel. The elasticity of the rolled condom also permits its extraction from the wrapping by means of slight distortion on being pulled to the side against the diagonal pre-cuts, should they resist.

The materials used are multi-layer laminates of aluminium and plastic, welded. The number and thickness of the materials composing these leaves are designed to ensure the impermeability of the wrapping against aggressive agents, in particular the wrapping should remain impermeable to air and UV, as well as resisting damage caused by rubbing, for example whilst being carried in clothing. The resistance of the weld joining the two planes of the envelope must be superior to the resistance to tearing of the pre-cut multi-layer leaf. The pre-cuts on the leaf must be such that they guide the tear in the wrapping along the desired pre-cut line, without burrs or residual torn parts which could cut the condom. The pre-cut line allows the creation of two clean-cut entities, without any materials becoming detached and falling onto the condom or elsewhere. The pre-cuts enter the top layer of the laminated leaf so as to assure tearing in the desired place, but on no account do they enter the lower layers which assure the integrity of the leaf and its impermeability to air and light; in this way the protective envelope is of equal quality to one made without pre-cut lines. The pre-cut is such that it ensures the tearing of the leaf follows the line. The opening will be clean, without burrs or residues, and complete in a single movement. The pre-cut circle is not complete in its full circumference so that the 'cap' part does not become completely detached and therefore the used wrapping forms a single item of waste.

The invention brings the following advantages:

Possibility of never mistaking the orientation when holding the wrapping

Possibility of opening in a single, simple, well-known movement

Possibility of never mistaking the orientation on taking the condom from its wrapping which is only done by grasping the vessel pointing the right way.

Possibility of never letting the condom slip from the wrapping when unwrapping.

The whole thing is achievable in the dark, identification of the right side being achievable by touch alone.

The wrapping is less off-putting, more fun, and favours the use of the condom which is good for both manufacturers (sales) and in its effect on public health.

Increased practical convenience: reduced unwrapping time.

Increased practical convenience: certainty, on opening the wrapping, of taking the condom in the right orientation without the necessity of checking or manipulation.

Increased practical and psychological convenience: reduction of psychological stress due to the certainty of applying the condom in the correct orientation. It is therefore possible to use the condom quickly, without the need to check its orientation, and so without the risk of putting it in contact the wrong way up then the right way up, which possibly contaminates both sides of the condom.

Increased practical convenience: removal of distracting effects, embarrassment and stress caused by wrappings which are not easily opened, by scattered small scraps of detached packaging, by condoms which slip from the grasp and which cannot be oriented in the dark.

Increased psychological comfort: removal of the stress caused by wrappings, opening which sometimes is attempted with the teeth at the risk of damage to the condom.

Increased practical convenience: by placing a fluorescent label or mark visible in the dark on the wrapping tab makes it possible not only always to have the condom in the right orientation on opening the wrapping, but also to find, without light, the wrapped condom near the place of use—reducing the time searching and fumbling in the dark, which is reassuring.

The invention claimed is:

1. Condom wrapping, comprising:
two superposed sections of film joined at the edges to form a container to hold a condom in a rolled-up state with a condom vessel in a normal position adjacent to one of the sections of film, the rolled-up condom having an external contour, the normal direction of unrolling the condom being towards the other section of film, the section of film adjacent to the condom vessel having a line of weakness outlining an opening area; and
means of gripping a part of film outlined by the line of weakness in such a way that the part of film can be torn in order to open the condom wrapping from the side of the condom vessel;
wherein the line of weakness is in a general shape corresponding approximately to the external contour of the condom, and the contour of the line is smaller than the external contour of the condom, in such a way as to ensure the retention of the condom in the condom wrapping after opening, whilst permitting easy extraction thereof, without unrolling, by drawing on the condom vessel.

2. The condom wrapping according to claim 1, wherein the contour of the line of weakness is 1%-10% smaller than the external contour of the condom.

3. The condom wrapping according to claim 1, wherein the line of weakness is a main line of weakness, the section of film adjacent to the condom vessel includes at least one additional line of weakness extending from the main line of weakness away from the opening area, radiating generally from the circular contour of the main line of weakness.

4. The condom wrapping according to claim 1, wherein the line of weakness is a main line of weakness, the section of film adjacent to the condom vessel includes four additional lines of weakness distributed evenly on the contour of the main line of weakness.

5. The condom wrapping according to claim 1, wherein the means of gripping are such that the identification by touch of the section of film adjacent to the condom vessel is permitted.

6. The condom wrapping according to claim 1, wherein the means of gripping include markings visible in the dark.

7. The condom wrapping according to claim 1, wherein the means of gripping include a tab connected to the part of the film outlined by the line of weakness, the tab being connected to that part of the film at the level of the line of weakness, so as to optimize purchase during the pulling of the tab.

8. The condom wrapping according to claim 7, wherein the tab is connected to the part of the film outlined by the line of weakness by gluing or soldering.

9. The condom wrapping according to claim 7, wherein the tab is a piece of film similar to the film of which the rest of the condom wrapping is made.

10. The condom wrapping according to claim 3, wherein the main and/or additional lines of weakness are created by means of one of the following processes: milling, weakening by laser beam, perforation, cutting, chemical treatment.

11. The condom wrapping according to claim 1, wherein contour of the line of weakness is incomplete, so as to retain, the part of the film outlined by the line of weakness attached to the rest of the condom wrapping after opening.

12. The condom wrapping according to claim 1, wherein the contour of the line of weakness is complete, so as to assure the separation of the part of the film outlined by the line of weakness after opening.

13. The condom wrapping according to claim 1, wherein the contour of the line of weakness and the contour of the condom are generally circular.

* * * * *